US009885652B2

(12) United States Patent
Papin et al.

(10) Patent No.: US 9,885,652 B2
(45) Date of Patent: Feb. 6, 2018

(54) MINIATURIZED MULTIWELL PLATE READER FOR PHENOTYPIC SCREENING

(71) Applicant: University of Virginia Patent Foundation, Charlottesville, VA (US)

(72) Inventors: Jason A. Papin, Charlottesville, VA (US); Paul A. Jensen, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/433,955

(22) PCT Filed: Oct. 8, 2013

(86) PCT No.: PCT/US2013/063867
§ 371 (c)(1),
(2) Date: Apr. 7, 2015

(87) PCT Pub. No.: WO2014/058869
PCT Pub. Date: Apr. 17, 2014

(65) Prior Publication Data
US 2015/0260642 A1    Sep. 17, 2015

Related U.S. Application Data

(60) Provisional application No. 61/710,961, filed on Oct. 8, 2012.

(51) Int. Cl.
*G01N 21/25* (2006.01)
(52) U.S. Cl.
CPC ................... *G01N 21/253* (2013.01)
(58) Field of Classification Search
CPC .................................................. G01N 21/253
(Continued)

(56) References Cited

U.S. PATENT DOCUMENTS

| 5,345,395 A | 9/1994 | Griner |
| 6,876,760 B1 * | 4/2005 | Vaisberg ............. G06K 9/0014 382/129 |

(Continued)

FOREIGN PATENT DOCUMENTS

| WO | WO-2007149361 A2 | 12/2007 |
| WO | WO-2014058869 A1 | 4/2014 |

OTHER PUBLICATIONS

Jensen, P.A. et al. (2015). "Miniaturized Plate Readers for Low-Cost, High-Throughput Phenotypic Screening." J Lab Automation. 20(1). 51-55.*

(Continued)

*Primary Examiner* — Jill Warden
*Assistant Examiner* — Jacqueline Brazin
(74) *Attorney, Agent, or Firm* — Schwegman Lundberg & Woessner, P.A.

(57) ABSTRACT

A multi-well plate reader including an emitter assembly having a plurality of emitters and a receptor assembly including a plurality of receptors separated by at least one spacer element such that a multi-well plate can be inserted between the emitter assembly and the receptor assembly. The emitters and receptors are paired and arranged in parallel arrays such that electromagnetic radiation can be transmitted through each well of the multi-well plate to a corresponding receptor to determine the opacity of the biological material contained within the well. Each well of the multi-well plate can be evaluated by a different emitter receptor pair allowing the entire multi-well plate to be efficiently monitored at a high throughput.

22 Claims, 10 Drawing Sheets

(58) Field of Classification Search
USPC .......................................................... 506/39
See application file for complete search history.

(56) References Cited

U.S. PATENT DOCUMENTS

| | | |
|---|---|---|
| 2003/0116497 A1* | 6/2003 | Carlson et al. ............... 210/435 |
| 2004/0168919 A1* | 9/2004 | Kurt et al. .................... 204/456 |
| 2005/0133724 A1 | 6/2005 | Hsieh et al. |
| 2006/0018833 A1* | 1/2006 | Murphy et al. ................ 424/9.2 |
| 2012/0182556 A1* | 7/2012 | Van Praet ............ G01N 21/253 356/440 |
| 2012/0190591 A1 | 7/2012 | Wohlstadter et al. |
| 2012/0252704 A1 | 10/2012 | Jaffe et al. |
| 2013/0109081 A1* | 5/2013 | Tsuchiya ................ G02B 21/30 435/286.1 |
| 2013/0143315 A1* | 6/2013 | Yamamoto ............. C12M 47/02 435/325 |
| 2015/0140570 A1* | 5/2015 | Fu ......................... C12M 23/22 435/7.1 |

OTHER PUBLICATIONS

"International Application Serial No. PCT/US2013/063867, International Search Report dated Feb. 28, 2014", 2 pgs.
"International Application Serial No. PCT/US2013/063867, Written Opinion dated Feb. 28, 2014", 8 pgs.
"European Application Serial No. 13846056.3, Extended European Search Report dated May 6, 2016", 9 pgs.

\* cited by examiner

MINIATURIZED MULTIWELL PLATE READER FOR PHENOTYPIC SCREENING

CLAIM OF PRIORITY

This patent application is a U.S. National Stage Filing under 35 U.S.C. 371 from International Patent Application Serial No. PCT/US2013/063867, filed on Oct. 8, 2013, and published on Apr. 17, 2014 as WO 2014/058869 A1, which claims the benefit of priority, under 35 U.S.C. Section 119(e), to Jason A. Papin, U.S. Provisional Patent Application Ser. No. 61/710,961, entitled "MULTIWELL PLATE READER FOR PHENOTYPIC SCREENING AND RELATED METHOD THEREOF," filed on Oct. 8, 2012, which is hereby incorporated by reference herein in its entirety.

STATEMENT REGARDING FEDERALLY SPONSORED RESEARCH OR DEVELOPMENT

This invention was made with government support under GM088244 awarded by the National Institutes of Health. The government has certain rights in the invention.

TECHNICAL FIELD

This document pertains generally, but not by way of limitation, to systems and related methods of monitoring growth of biological samples contained in multi-well plates.

BACKGROUND

Biological research or testing, such as phenotypic screening, frequently involves growing collected or prepared biological samples in an incubator to evaluate the growth characteristics of the biological sample or create sufficient biological material for further evaluation. Multi-well or microtiter plates are a standard tool used to simultaneously handle and grow a plurality of biological samples. The simultaneous growth provided by multi-well plates is particularly advantageous as the growth time necessary for biological samples to reach the requisite size for evaluation ranges from several hours to several days. With certain biological samples, the growth of the biological sample is measured by inserting the multi-well plate into a reader. The reader includes a radiation emitter that applies visible light, infrared energy or other electromagnetic radiation to the biological sample in each well and measures the resulting optical density, absorbance, fluorescence or luminescence of the biological sample to determine the size and other features of the biological sample.

The advantages provided by multiple sample wells are offset by the challenge of simultaneously or efficiently monitoring the growth of the plurality of biological samples. As most biological samples require similar growth environments, a single incubator can often simultaneously provide the appropriate growth environment for each well in a multi-well plate or a plurality of multi-well plates. However, a reader must evaluate each well individually as the biological samples may grow at different rates. Accordingly, presently available readers have moveable radiation emitters positioned on mechanical arms or assemblies that move the emitter across the face of the multi-well plate to align the emitter with each well and apply the appropriate electromagnetic radiation to each well individually. The moving and sequentially operated emitter provides precise measurement of the biological sample, but substantially slows the evaluation process as the moving emitter must be continually repositioned. Similarly, the moving components must be precisely calibrated to align the emitter with the wells, which can have a mouth smaller than twelve millimeters in diameter. As a result, readers for monitoring growth multi-well plates are often very expensive to purchase and maintain.

A similar drawback is that presently available readers require the multi-well plate to be removed from the incubator and inserted into a special slot or tray. The slot or tray positions the multi-well plate such that the wells are aligned with positions pre-programmed into the movable emitter. As a result, if the multi-well plate is misaligned with the programmed position the measurements could be inconclusive or erroneous. As the multi-well plate must be repeatedly removed from the incubator and inserted into the reader over the course of the growth time, the risk of error is compounded. In addition, as the growth time can span hours or days, the continual monitoring of the multi-well plate can become tedious further increasing the likelihood that the multi-well plate will be improperly inserted and positioned due to operator error.

OVERVIEW

The present inventors have recognized, among other things, that the problem to be solved includes the inability to efficiently monitor the growth of a plurality of biological samples in the wells of a multi-well plate and in particular without removing the multi-well plate from the incubator. Similarly, the inventors have also recognized that the mechanical complexity associated with mechanically moving a single radiation emitter across the multi-well plate to individually evaluate each well slows the overall evaluation process and creates a likelihood of inconclusive or incorrect test results. Furthermore, the inventors have recognized that these problems can be solved in part by a multi-well plate reader having an emitter assembly and a receptor assembly separated by at least one spacer element such that a multi-well plate can be inserted between the emitter assembly and the receptor assembly.

In an example, the emitter assembly comprises a plurality of electromagnetic emitters each operable to transmit electromagnetic radiation along an optical path. Correspondingly, the receptor assembly comprises a plurality of receptors each of which is paired with one of the emitters and positioned in the optical path of the paired emitter to receive the electromagnetic radiation transmitted by the corresponding emitter. Each emitter-receptor pair is positioned such that optical path intersects with a well of the multi-well plate when the multi-well plate is inserted between the emitter assembly and the receptor assembly. In operation, each emitter is operated to transmit electromagnetic radiation at a predetermined intensity through the corresponding well and any biological sample therein to the corresponding receptor. The receptor measures the intensity of the electromagnetic radiation that reaches the receptor to calculate the optical density of the biological sample. The present inventors have recognized that the optical density of the biological samples correlates to the amount of biological material contained in the well and accordingly can be monitored over time to evaluate the growth of the biological sample.

In an example, the plurality of emitters and plurality of receptors are arranged in parallel planar arrays positioned such that at least one optical path of each emitter intersects one of the wells of a multi-well plate inserted between the emitters and receptors. In this configuration, each emitter-receptor pair is operated sequentially to investigate the optical density of the biological samples contained within each well. As each emitter is pre-aligned with a well, each well can be sequentially illuminated without the downtime required to mechanically move a single emitter into alignment with the next well. In addition, as the optical density measurement only requires a brief illumination of the well, the wells of the multi-well plate can be evaluated in rapid succession. In an example, the evaluation time required to evaluate the optical density of a biological sample in each well is about 10 to about 20 milliseconds (ms).

In an example, the emitter assembly includes a first alignment plate and the receptor assembly includes a second alignment plate. The first alignment plate structural supports and positions the array of emitters parallel to the multi-well plate and includes a first window through which the emitted radiation is directed. The second alignment plate structural supports and positions the array of receptors parallel to the multi-well plate and includes a second window through which the emitted radiation is received. The multi-well plate assembly is positionable within an incubator and is operable to monitor the optical density of the biological samples from within the incubator without removing the multi-well plate assembly from the incubator. In an example, the multi-well plate assembly also includes at least one footing element supporting the receptor and emitter assemblies. Each footing element includes a mounting feature for securing the multi-well plate assembly to a shaker plate or other structure within the incubator to mount the multi-well plate reader within the incubator. Similarly, the mounting feature is securable to a corresponding feature on an adjacent multi-well plate assembly such that a plurality of multi-well plate assemblies can be stacked within the incubator.

In an example, the multi-well plate assembly includes an onboard controller having a microprocessor for processing the opacity measurements received from the plurality of receptors. The onboard controller is operably connected to the plurality of emitters and adapted to sequentially operate each emitter. The multi-well plate assembly also includes a networking component for wired or wireless communication with a receiving unit such as a computer or a dedicated controller. The networking component is operable to transmit the opacity measurements processed by the microprocessor to the receiving unit such that the measurements can be displayed visually or further evaluated. Alternatively, the receiving unit is operable to transmit operating instructions for the operation of the plurality of emitters to the on board controller via the networking component.

In an example, a plurality of multi-well plate assembly are networked to a single receiving unit such that the single receiving unit operates to control the operation of the plurality of multi-well plate assemblies as well as compile and organize the opacity measurements from each multi-well plate assembly. Similarly, in an example, a plurality of multi-well plate assemblies is networked to at least one router that is networked to the single receiving unit. In this configuration, the multi-well plate assemblies are arranged in a branching network via the routers instead of each being directly linked to the multi-well plate assembly.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
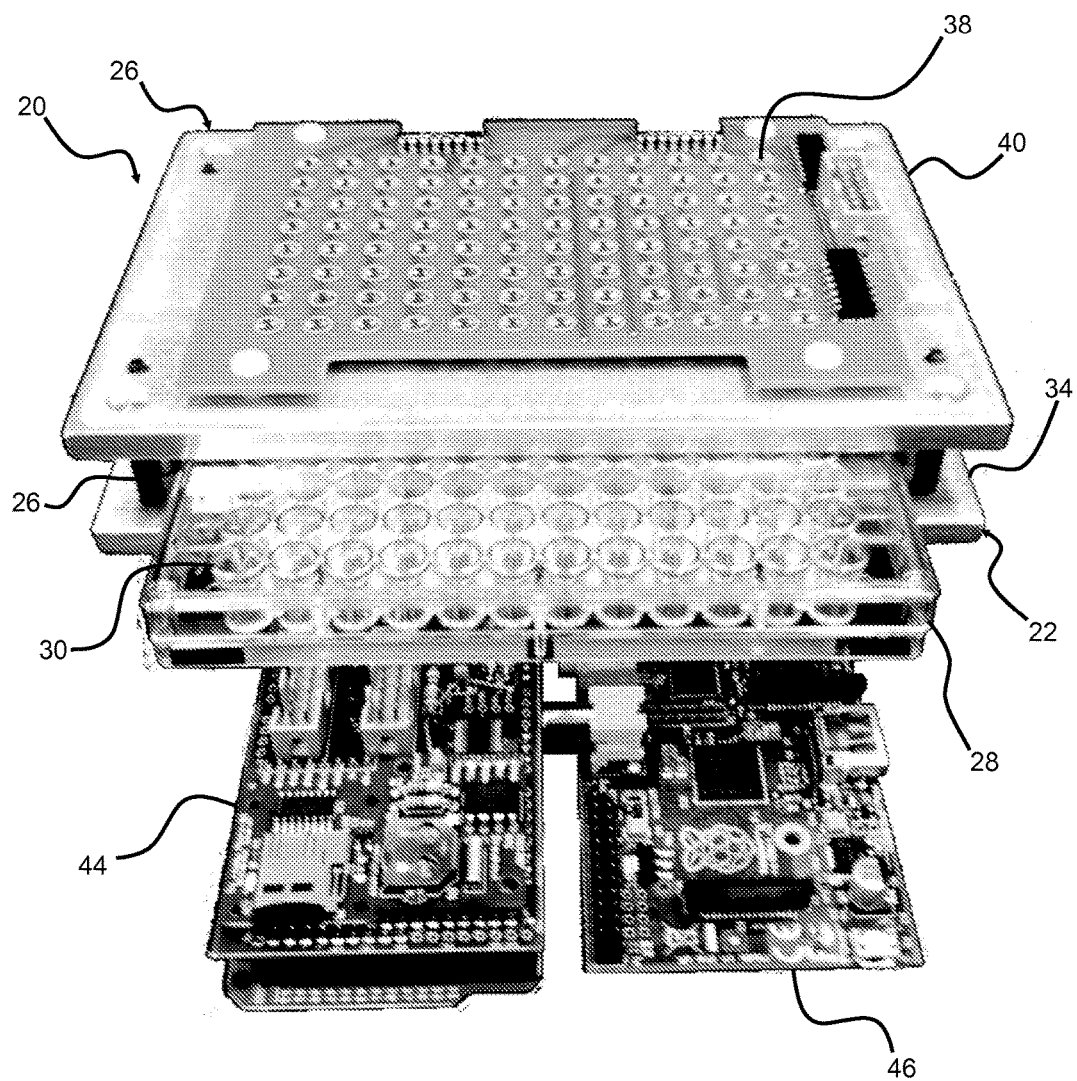
FIG. 1 is a partially exploded perspective view of a multi-well plate reader and a multi-well plate according to an example of the present disclosure.

As depicted in FIGS. 1-6, a multi-well plate reader 20, according to at least one example of the present subject matter, includes an emitter assembly 22, a receptor assembly 24 and at least one spacer element 26. The spacer element 26 extends between the emitter assembly 22 and the receptor assembly 24 to define a slot or space between the emitter assembly 22 and the receptor assembly 24 for receiving a multi-well plate 28 having a plurality of wells 30. As depicted, the multi-well plate 28 comprises a 96 well plate having cylindrical wells, but can comprise other presently available multi-well plate 28 design. The multi-well plate 28 for use with the multi-well plate reader 20 comprises a fully or semi-transparent material. The description of the multi-well plate 28 is not intended to be limiting, but rather to aid in the description of the multi-well plate reader 20. For the purposes of this disclosure, a multi-well plate reader 20 describes the emitter assembly 22, receptor assembly 24 and at least one spacer element 26 and a multi-well plate assembly refers to the multi-well plate reader 20 with the multi-well plate positioned in the slot or space.

Figure 2:
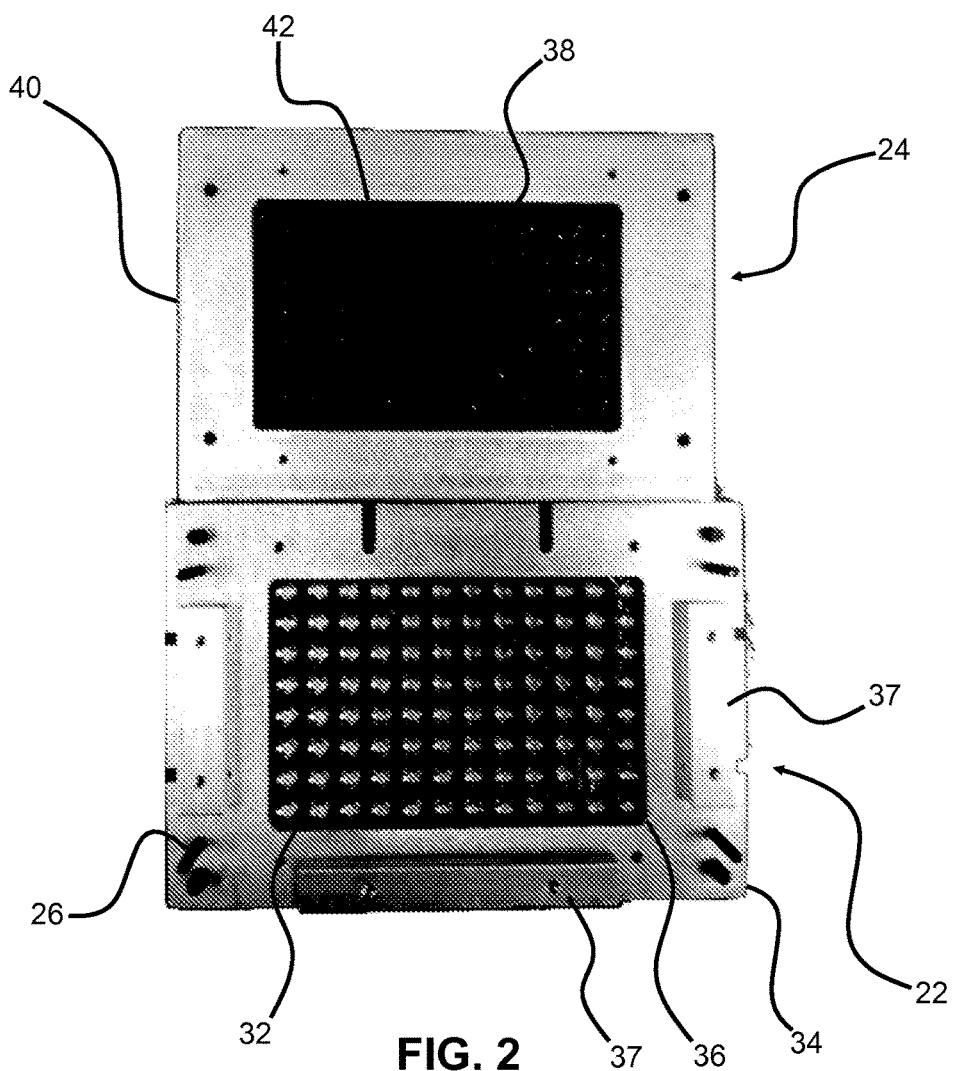
FIG. 2 is top view of a multi-well plate reader according to an example of the present disclosure with the receptor assembly rotated to expose the emitter assembly.
Figure 3:
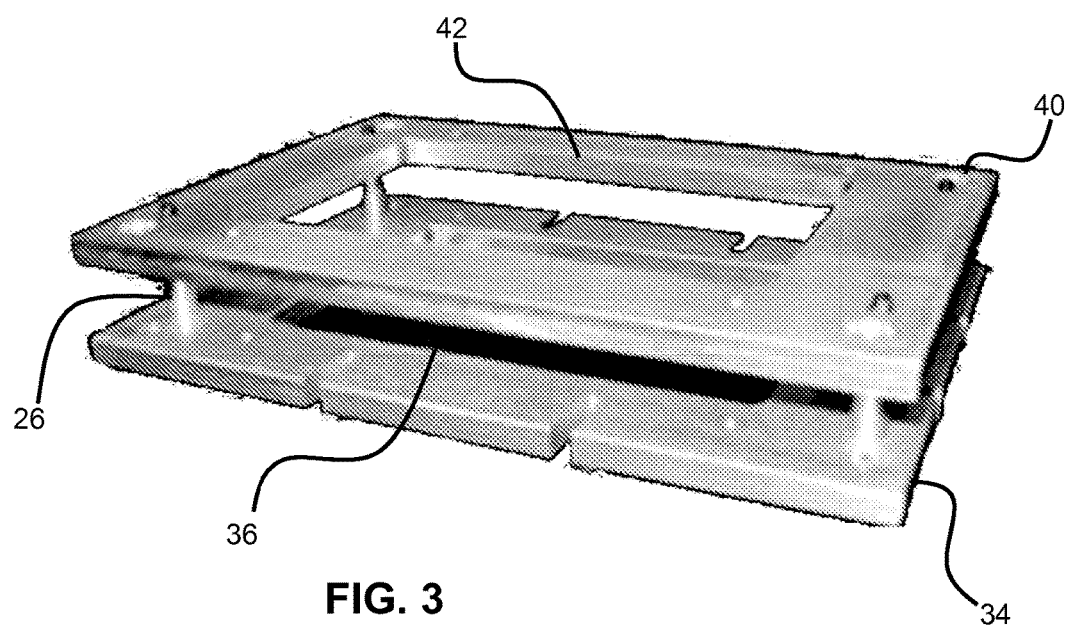
FIG. 3 is a perspective view of a first alignment plate and a second alignment plate separated by a plurality of spacer elements of a multi-well plate reader according to an example of the present disclosure.
Figure 4:
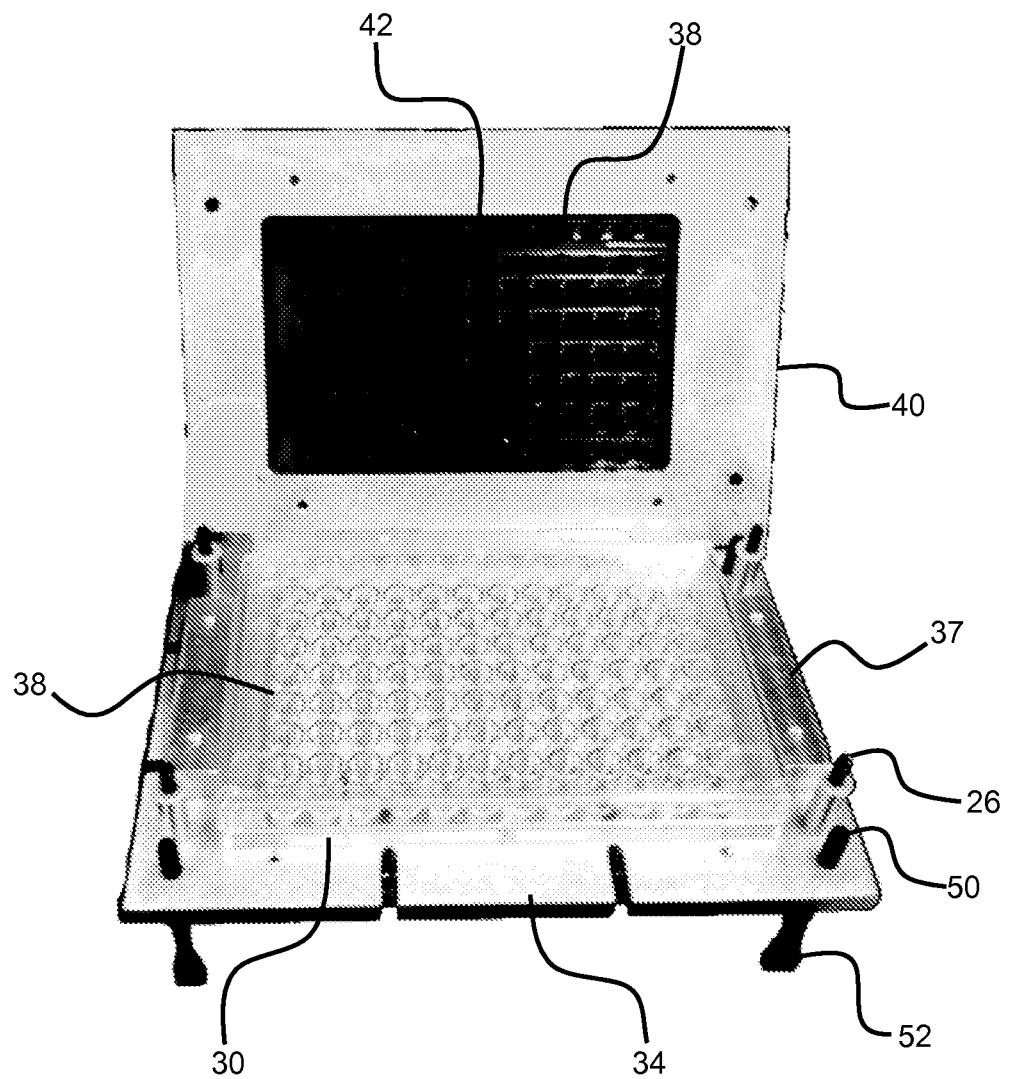
FIG. 4 is a perspective view of a multi-well plate reader according to an example of the present disclosure, wherein a multi-well plate is positioned within the multi-well plate reader and the receptor assembly rotated to expose the emitter assembly.
Figure 5:
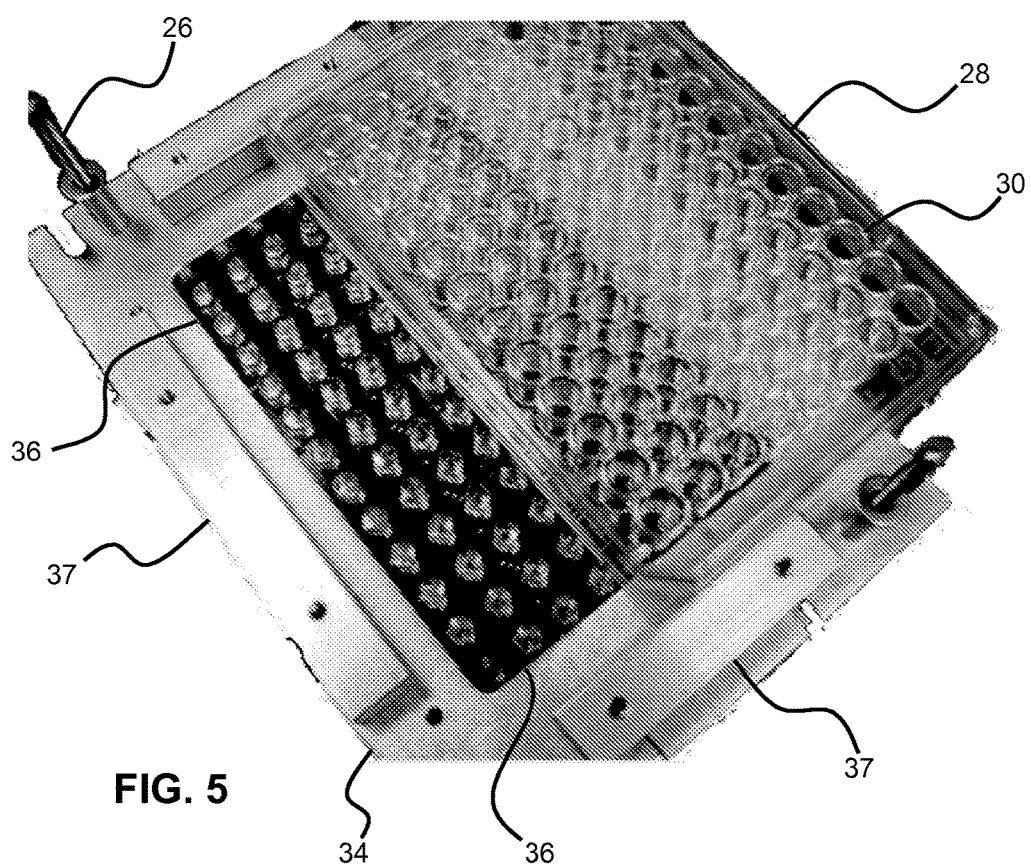
FIG. 5 is a perspective view of an emitter assembly of a multi-well plate reader according to an example of the present disclosure and a multi-well plate.

As depicted in FIGS. 2 and 4, the emitter assembly 22 includes a plurality of electromagnetic emitters 32. The electromagnetic emitters 32 are each operable to emit electromagnetic radiation along an optical path. The electromagnetic emitters 32 are arranged in a planar array such that the optical paths of the plurality of the electromagnetic emitters 32 are generally parallel. In an example, the electromagnetic emitter 32 comprises an infrared light emitting diode. In other examples, the infrared light emitting diode comprises a peak emission between about 800 and 900 nanometers ("nm"). In yet other examples, the infrared light emitting diode comprises a peak emission about 840 nm.

In an example, the plurality of electromagnetic emitters 32 is grouped into a plurality of emitter clusters each including two or more emitters 32. In this configuration, the plurality of emitter clusters are similarly arranged in a planar array, wherein each cluster comprises emitters 32 adapted to emit different types of electromagnetic radiation including, but not limited to infrared radiation, ultraviolet radiation and visible light.

In an example, the emitter assembly 22 also includes a first alignment plate 34 defining a first window 36. The plurality of electromagnetic emitters 32 is mounted to the first alignment plate 34 such that the emitters 32 are oriented to direct the electromagnetic radiation through the first window 36. In an example, the first alignment plate 34 also includes at least one retention feature 37 positioned to engage an interested multi-well plate 28 and align wells 30 of the multi-well plate 28 with the first window 36.

Figure 7:
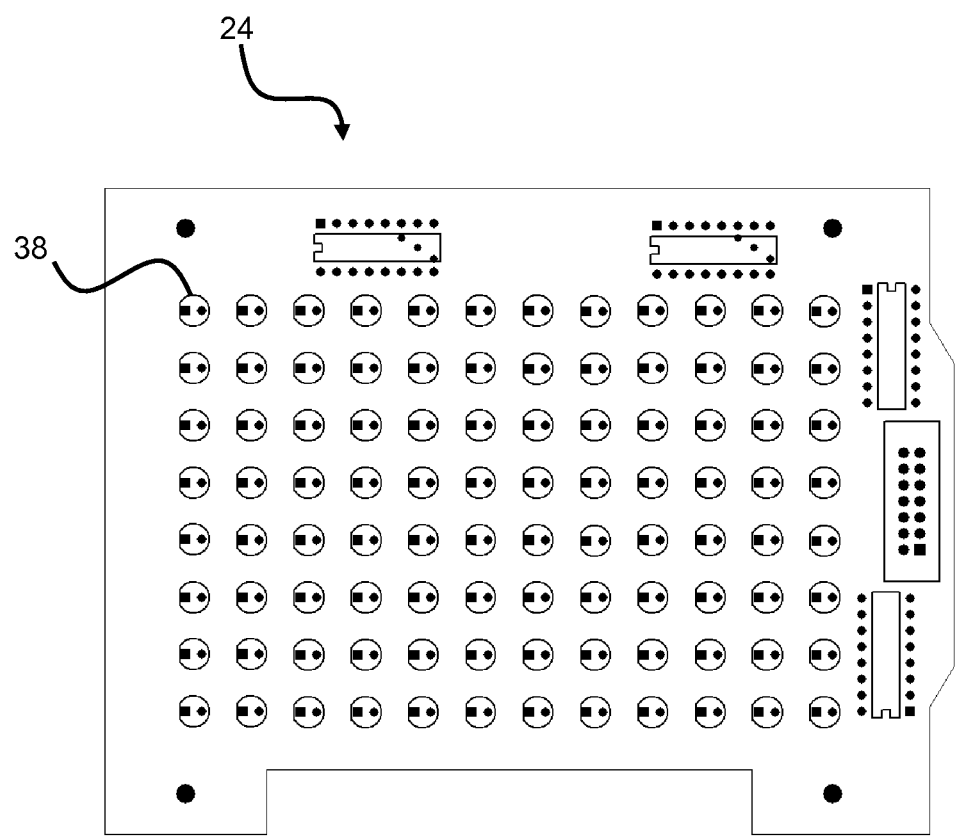
FIG. 7 is a schematic view of a plurality of receptors of a multi-well plate reader according to an example of the present disclosure.
Figure 8:
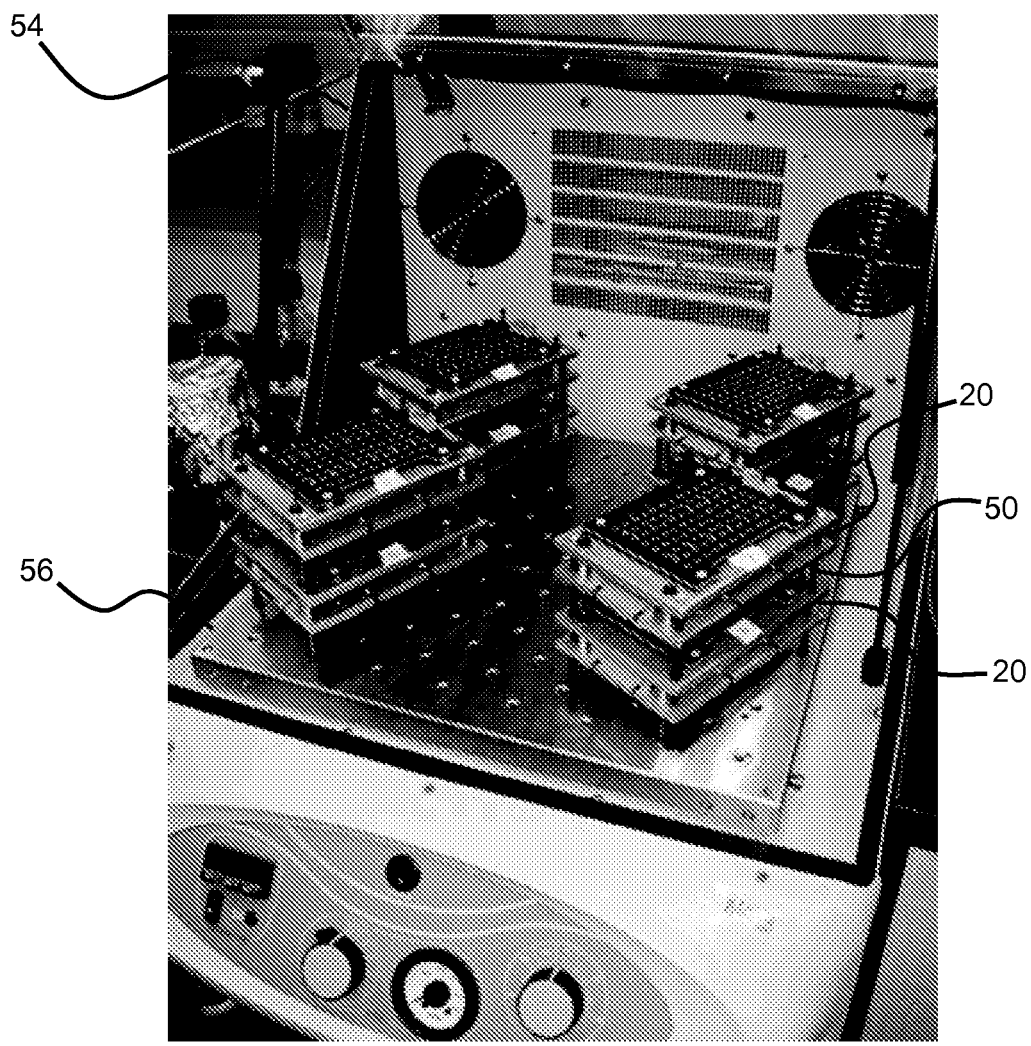
FIG. 8 is a perspective view of a plurality of multi-well plate readers according to an example of the present disclosure positioned within an incubator.

As depicted in FIGS. 2, 4 and 7, the receptor assembly 24 includes a plurality of receptors 38. As depicted in FIG. 7, the receptors 38 are arranged in a planar array parallel to the planar array of emitters 32. Each receptor 38 is paired with a corresponding emitter 32 and positioned to intersect the optical path of the emitter 32 such that the receptor 38 receives and measures the intensity of the electromagnetic radiation emitted by the corresponding emitter 32 that is actually received by the receptor 38. In an example, each receptor 38 comprises a phototransistor detector having an absorption spectrum paired to the type of electromagnetic radiation emitted by the emitter 32.

In an example, the plurality of electromagnetic receptors 38 is grouped into a plurality of receptors 38 each including two or more receptors 38. In this configuration, the plurality of receptors are similarly arranged in a planar array corresponding to a planar array of emitter clusters, wherein each cluster comprises different receptors 38 adapted to receive different types of electromagnetic radiation including, but not limited to infrared radiation, ultraviolet radiation and visible light.

In an example, the receptor assembly 24 also includes a second alignment plate 40 defining a second window 42. The plurality of receptors 38 is mounted to the second alignment plate 40 such that the receptors 38 are oriented to receive electromagnetic radiation through the second window 40. In an example, the second alignment plate 40 comprises a rectangular shape and at least one spacer element 26 is positioned at each corner of the second alignment plate 40 and extends to the corresponding corners of the first alignment plate 34 to align the first window 36 with the second window 42.

As depicted in FIGS. 1-6, the multi-well plate 28 is positioned within the slot defined between the emitter assembly 22 and the receptor assembly 24 such that each well 30 intersects at least one of the optical paths of the emitter-receptor pairs. In an example, the optical paths of each emitter cluster intersect a single well 30 of the multi-well plate 28. In operation, each emitter 32 is operable to transmit electromagnetic radiation along the optical path through the corresponding well 30 and to the paired receptor 38. In an example, each emitter 32 in the plurality of emitters 32 is operated sequentially to provide consistent testing conditions for each well 30. As a biological material within the well 30 grows and the optical opacity increases, the amount of electromagnetic radiation reaching the receptor 38 decreases. In an example, the receptor assembly 24 further comprises a microprocessor 42 for comparing the intensity of electromagnetic radiation emitted by emitter 32 to the measured intensity of electromagnetic radiation received by the receptor assembly 24 to determine the optical opacity of the biological sample in the well 30. The optical density of the biological sample in each well 30 provides an estimate of the present size of the biological material in the biological sample and correspondingly the growth of the biological sample.

Figure 9:
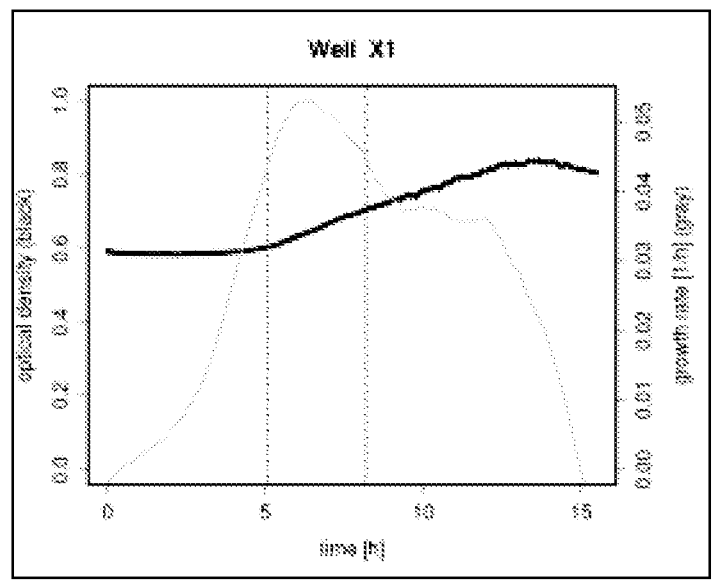
FIG. 9 is a representative display of opacity measurement of a biological sample over time and compared to the growth of the biological sample.
Figure 10:
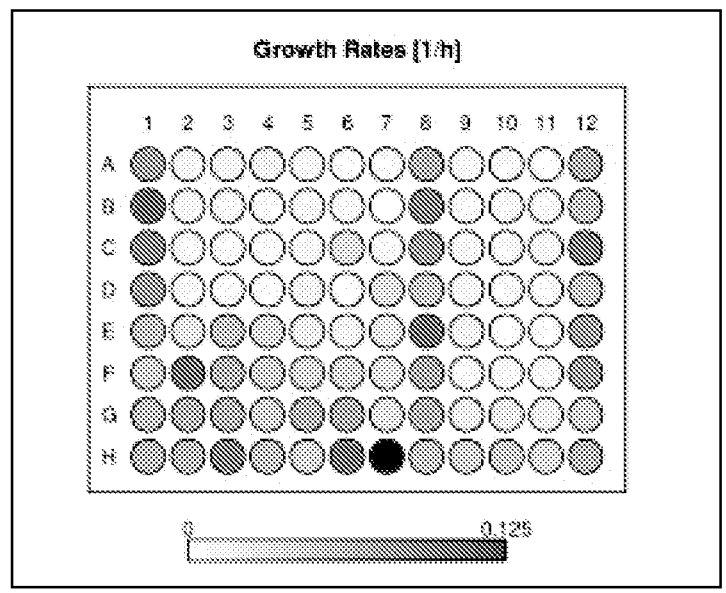
FIG. 10 is a representative display of opacity measurements of a plurality of wells of a multi-well plate taken by a multi-well plate reader according to an example of the present disclosure.

In an example, the multi-well plate reader 20 further includes an onboard controller 44 having at least a microprocessor and a networking component 46. The onboard controller 44 is operably linked to each emitter 32 and operable to sequentially operate each emitter 32 to evaluate the opacity of the biological samples contained within the wells 30. The microprocessor is operably linked to each receptor 38 to collect and process the opacity measurements from each receptor 38. The processed opacity measurements are then transmitted wirelessly or via a wired connection to a receiving unit. The network adapter can comprise a wired Ethernet adapter, wireless adapter, radio antenna, Bluetooth adapter or other means of wired or wireless digital communication. Similarly, the receiving unit can comprise a personal computer, a dedicated controller, offsite server or other computer system for receiving the opacity measurements from the microprocessor of the receptor assembly 24. The opacity measurements can then be aggregated and plotted by the receiving unit to display the present growth of the biological samples in each well as depicted in FIG. 9 or plotted over time to track the growth of the biological sample over time as depicted in FIG. 10. Similarly, the receiving unit is also operable to transmit operating instructions to the onboard controller 44 to change the operation of the plurality of emitters 32 or manually initiate operation of emitters 32.

Figure 11:
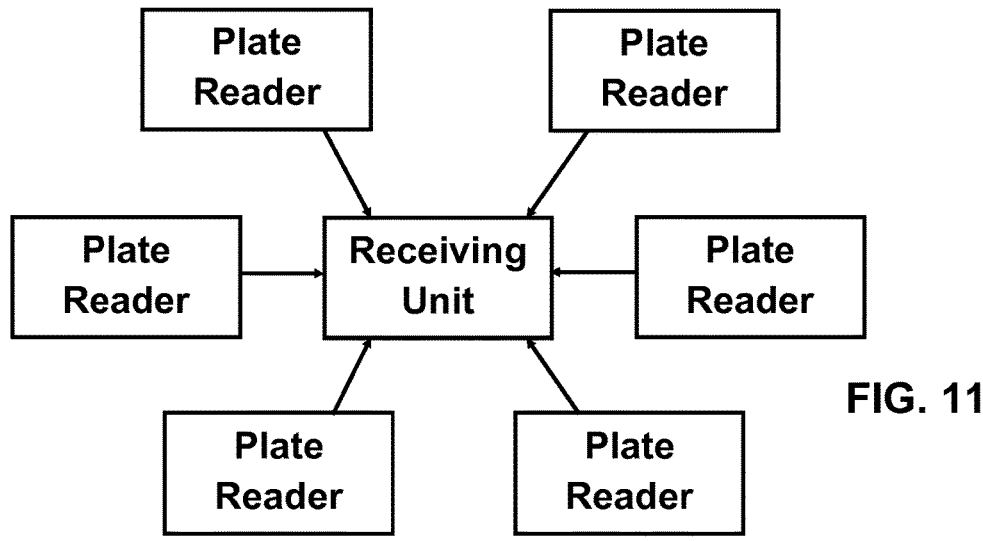
FIG. 11 is a schematic diagram of a networked plurality of multi-well plate readers according to an example of the present disclosure.
Figure 12:
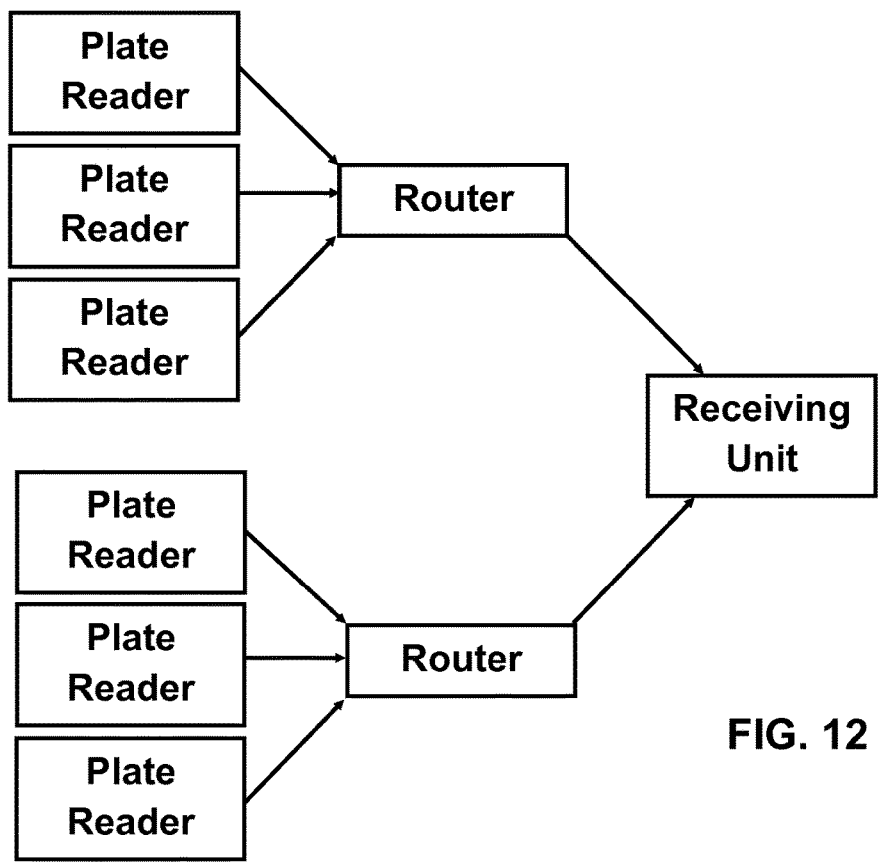
FIG. 12 is a schematic diagram of a networked plurality of multi-well plate readers according to an example of the present disclosure.

As depicted in FIG. 11, in an example, a plurality of multi-well plate readers 20 are networkable to a single receiving unit such that the single receiving unit operates as a central controller for the multi-well plate readers 20 and for aggregating the opacity data from the multi-well plate readers 20. As depicted in FIG. 12, in another example, a plurality of multi-well plate readers 20 is networked to one or more router that is networked to the receiving unit. In this configuration, the multi-well plate readers 20 are arranged in a branched configuration via the routers rather than individually linked directly to the receiving unit.

Figure 6:
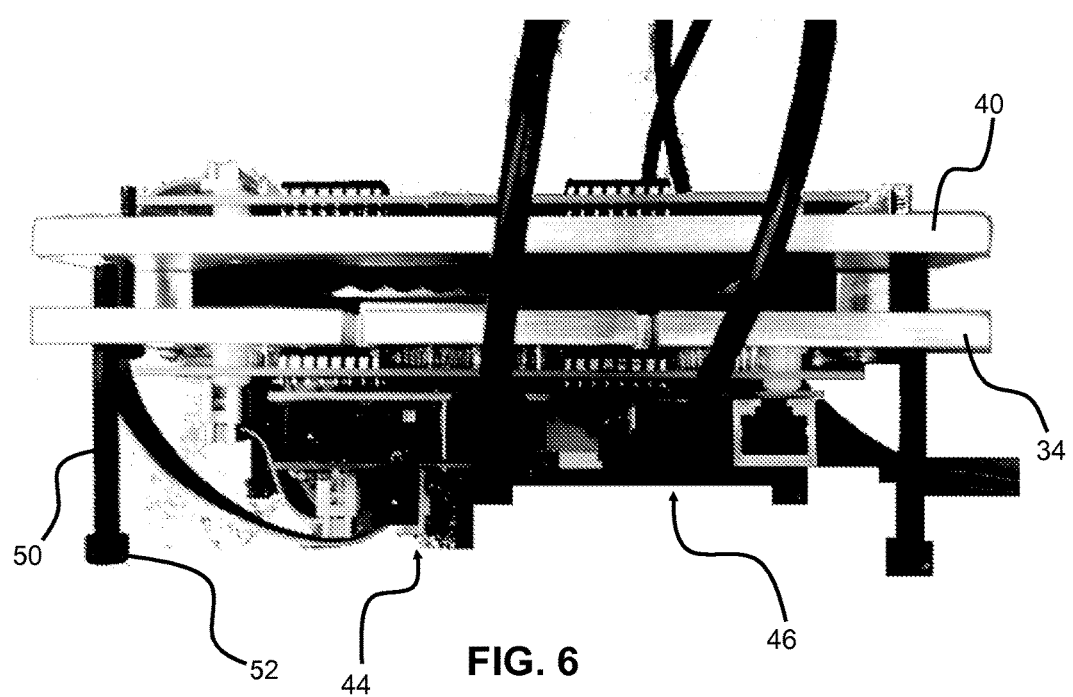
FIG. 6 is a side view of a multi-well plate reader according to an example.

As depicted in FIG. 6, the multi-well plate reader 20 also includes a storage media drive. The storage media drive is capable of receiving and writing information on storage media including, but not limited to SD memory cards, micro-SD memory cards, flash memory and other forms of storage media. In this configuration, the storage media drive allows the multi-well plate reader 20 to record the measured opacity data on a storage media, such as a non-transitory computer-readable storage medium.

As depicted in FIGS. 1-6, in an example, the multi-well plate reader 20 further comprises at least one footing element 50 and at least one coupling element 52 securable to an adjacent multi-well plate reader 20. In this configuration, a plurality of multi-well plate readers 20 can be stacked and secured together into a single assembly. In an example, the coupling element 52 is securable to a structural feature of an incubator 54 such as the shaker plate 56 to secure the multi-well plate reader 20 or plurality of multi-well plate 20 readers to the incubator 54 as depicted in FIG. 7.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A multi-well plate reader, comprising:
an emitter assembly including a plurality of electromagnetic emitters mounted to a first alignment plate and oriented to transmit electromagnetic radiation through a first window defined by the first alignment plate;
a receptor assembly including a plurality of receptors mounted to a second alignment plate and oriented to receive electromagnetic radiation through a second window defined by the second alignment plate;
a spacer element separating and positioning the emitter assembly to the receptor assembly to define a plate slot for receiving a multi-well plate between the first alignment plate and the second alignment plate and align the multi-well plate with the first and second windows,
a microprocessor operably coupled to one of the first alignment plate and the second alignment plate and operably linked to each receptor; and
a footing element extending from at least one of the first alignment plate and the second alignment plate, the footing element comprising a coupling element is configured to couple the multi-well plate to at least one of a structural feature within an incubation chamber of an incubator or a second multi-well plate reader;
wherein each electromagnetic emitter is operable to transmit electromagnetic radiation at a predetermined intensity to one receptor of the plurality of receptors along a generally linear optical path through the first window, traversing the plate slot, and through the second window, wherein the microprocessor operably coupled to one of the first alignment plate and the second alignment plate and is programmed to determine real time growth of a biological sample in the multi-well plate during incubation of the multi-well plate within the plate slot by evaluating changes between at least two received intensity values measured by the corresponding receptor.

2. The multi-well plate reader of claim 1, wherein the plurality of electronic emitters and the plurality of receptors are arranged in parallel planar arrays separated by the plate slot.

3. The multi-well plate reader of claim 1, wherein each electromagnetic emitter comprises an infrared light emitting diode, wherein each infrared light emitting diode is adapted to transmit infrared radiation at the predetermined intensity.

4. The multi-well plate reader of claim 3, wherein each infrared light emitting diode comprises a peak emission between 800 nm and 900 nm.

5. The multi-well plate reader of claim 3, wherein each receptor comprises a phototransistor detector for measuring the received intensity of infrared radiation received from the corresponding electromagnetic emitter.

6. The multi-well plate reader of claim 1, wherein the emitter assembly further comprises a controller operably coupled to each emitter to initiate each electromagnetic emitter to emit electromagnetic radiation.

7. The multi-well plate reader of claim 6, wherein the controller operates the plurality of electromagnetic emitters sequentially.

8. A multi-well plate system, comprising:
an incubator having a structural feature positioned within an incubator chamber;
a transparent multi-well plate including a plurality of wells for receiving biological samples;
a multi-well plate reader, comprising:
an emitter assembly including a plurality of electromagnetic emitters mounted to a first alignment plate and oriented to transmit electromagnetic radiation through a first window defined by the first alignment plate;
a receptor assembly including a plurality of receptors mounted to a second alignment plate and oriented to receive electromagnetic radiation through a second window defined by the second alignment plate;
a spacer element separating and positioning the emitter assembly to the receptor assembly to define a plate slot for receiving the multi-well plate between the first and second alignment plates and aligning the multi-well plate with the first and second windows;
a microprocessor operably coupled to one of the first alignment plate and the second alignment plate and operably linked to each receptor; and
a coupling element positioned on at least one of the first alignment plate and the second alignment plate, the coupling element is configured to couple the multi-well plate to at least one of the structural feature of the incubator or a second multi-well plate reader;
wherein each electromagnetic emitter is operable to transmit electromagnetic radiation at a predetermined intensity to one receptor of the plurality of receptors along a generally linear optical path through the first window plate, traversing the plate slot, and through the second window plate such that each linear optic path intersects at least one of the wells of the plurality of wells to pass through the biological sample contained therein,
wherein the microprocessor is programmed to determine real time growth of the biological sample within at least one of the wells during incubation of the multi-well plate within the multi-well plate reader by evaluating changes between at least two received intensity values measured by the corresponding receptor.

9. The multi-well plate system of claim 8, wherein the plurality of electronic emitters and the plurality of receptors are arranged in planar arrays each parallel to the multi-well plate.

10. The multi-well plate system of claim 9,
wherein the first alignment plate contacts the multi-well plate to maintain parallel alignment of the multi-well plate with the arrayed plurality of electronic emitters.

11. The multi-well plate system of claim 9,
wherein the spacer element operably couples the first alignment plate to the second alignment plate;
wherein the second alignment plate contacts the multi-well plate to maintain parallel alignment of the multi-well plate with the arrayed plurality of electronic emitters.

12. The multi-well plate system of claim 8, wherein each electromagnetic emitter comprises an infrared light emitting diode, wherein each infrared light emitting diode is adapted to transmit infrared radiation at the predetermined intensity.

13. The multi-well plate system of claim 12, wherein each infrared light emitting diode comprises a peak emission between 800 nm and 900 nm.

14. The multi-well plate system of claim 12, wherein each receptor comprises a phototransistor detector for measuring the received intensity of infrared radiation received from the corresponding electromagnetic emitter.

15. The multi-well plate system of claim 8, wherein the emitter assembly further comprises a controller operably coupled to each emitter to initiate each electromagnetic emitter to emit electromagnetic radiation.

16. The multi-well plate system of claim 15, wherein the controller operates the plurality of electromagnetic emitters sequentially.

17. The multi-well plate reader of claim 1, wherein the microprocessor is programmed to determine growth of the biological sample by measuring the change in the received intensity over a predetermined period of time.

18. The multi-well plate reader of claim 17, wherein the growth of biological sample obstructs transmitted electromagnetic radiation through the plate slot to provide an intermediate intensity at the receptor.

19. The multi-well plate system of claim 8, the microprocessor is programmed to determine growth of the biological sample by measuring the change in the received intensity over a predetermined period of time.

20. The multi-well plate system of claim 19, wherein the growth of biological sample obstructs transmitted electromagnetic radiation through the plate slot to provide an intermediate intensity at the receptor.

21. The multi-well plate system of claim 1, wherein the structural feature is a shaker plate;
wherein the coupling element prevents sliding of the multi-well plate reader and multi-well plate received therein during oscillation of the shaker plate.

22. The multi-well plate system of claim 8, wherein the structural feature is a shaker plate;
wherein the coupling element prevents sliding of the multi-well plate reader and multi-well plate received therein during oscillation of the shaker plate.

* * * * *